(12) United States Patent
McClinchey et al.

(10) Patent No.: US 11,096,350 B2
(45) Date of Patent: *Aug. 24, 2021

(54) CANOLA INBRED G00555

(71) Applicant: PIONEER HI-BRED INTERNATIONAL, INC., Johnston, IA (US)

(72) Inventors: Scott McClinchey, East Garafraxa (CA); Jayantilal Devabhai Patel, Thornhill (CA)

(73) Assignee: PIONEER HI-BRED INTERNATIONAL, INC.

( * ) Notice: Subject to any disclaimer, the term of this patent is extended or adjusted under 35 U.S.C. 154(b) by 98 days.

This patent is subject to a terminal disclaimer.

(21) Appl. No.: 16/662,849

(22) Filed: Oct. 24, 2019

(65) Prior Publication Data
US 2021/0120756 A1 Apr. 29, 2021

(51) Int. Cl.
*A01H 6/20* (2018.01)
*A01H 5/10* (2018.01)

(52) U.S. Cl.
CPC ............... *A01H 6/202* (2018.05); *A01H 5/10* (2013.01)

(58) Field of Classification Search
None
See application file for complete search history.

(56) References Cited

U.S. PATENT DOCUMENTS 9,179,634 B2 11/2015 Patel
9,210,857 B1 * 12/2015 Ripley .................... A01H 5/10

OTHER PUBLICATIONS

U.S. Appl. No. 16/662,961 for Canola Variety 16GG0331R, filed Oct. 24, 2019.
U.S. Appl. No. 16/663,036 for Canola Variety 17GG0028L, filed Oct. 24, 2019.
U.S. Appl. No. 16/663,049 for Canola Variety 16GG0344L, filed Oct. 24, 2019.
U.S. Appl. No. 16/663,059 for Canola Variety 16GG0337L, filed Oct. 24, 2019.

* cited by examiner

*Primary Examiner* — Matthew R Keogh

(57) ABSTRACT

A novel canola variety designated G00555 and seed, plants and plant parts thereof. Methods for producing a canola plant that comprise crossing canola variety G00555 with another canola plant. Methods for producing a canola plant containing in its genetic material one or more traits introgressed into G00555 through backcross conversion and/or transformation, and to the canola seed, plant and plant part produced thereby. Hybrid canola seed, plant or plant part produced by crossing the canola variety G00555 or a locus conversion of G00555 with another canola variety.

20 Claims, No Drawings

CANOLA INBRED G00555

BACKGROUND

A novel rapeseed line designated G00555 is the result of years of careful breeding and selection. Since such variety is of high quality and possesses a relatively low level of erucic acid in the vegetable oil component and a relatively low level of glucosinolate content in the meal component, it can be termed "canola" in accordance with the terminology commonly used by plant scientists.

SUMMARY

Provided a novel *Brassica napus* line designated G00555. Seed of canola line G00555, plants of canola line G00555, plant parts of canola line G00555, and processes for making a canola plant that comprise crossing canola line G00555 with another *Brassica* plant are provided. Also provided is G00555 with cytoplasm comprising a gene or genes that cause male sterility. Processes for making a plant containing in its genetic material one or more traits introgressed into G00555 through backcross conversion and/or transformation, and to the seed, plant and plant parts produced thereby are provided. A hybrid canola seed, plant or plant part can be produced by crossing the line G00555 or a locus conversion of G00555 with another *Brassica* plant.

DEFINITIONS

In the description and examples which follow, a number of terms are used. The following definitions and evaluation criteria are provided.

Anther Fertility. The ability of a plant to produce pollen; measured by pollen production. 1=sterile, 9=all anthers shedding pollen (vs. Pollen Formation which is amount of pollen produced).

Anther Arrangement. The general disposition of the anthers in typical fully opened flowers is observed.

Chlorophyll Content. The typical chlorophyll content of the mature seeds is determined by using methods recommended by the Western Canada Canola/Rapeseed Recommending Committee (WCC/RRC). 1=low (less than 8 ppm), 2=medium (8 to 15 ppm), 3=high (greater than 15 ppm). Also, chlorophyll could be analyzed using NIR (Near Infrared) spectroscopy as long as the instrument is calibrated according to the manufacturer's specifications.

CMS. Abbreviation for cytoplasmic male sterility.

Cotyledon. A cotyledon is a part of the embryo within the seed of a plant; it is also referred to as a seed leaf. Upon germination, the cotyledon may become the embryonic first leaf of a seedling.

Cotyledon Length. The distance between the indentation at the top of the cotyledon and the point where the width of the petiole is approximately 4 mm.

Cotyledon Width. The width at the widest point of the cotyledon when the plant is at the two to three-leaf stage of development. 3=narrow, 5=medium, 7=wide.

CV %: Abbreviation for coefficient of variation.

Cytoplasmic Conversion. A plant that has been developed by transferring the cytoplasm of a plant to a variety of interest. This can be done through crossing the variety of interest to a plant that has the desired cytoplasm and backcrossing to the variety of interest. The cytoplasm will be transferred through the female parent. The result would be the genome of the variety of interest with the cytoplasm of another plant, generally the cytoplasm from the other plant will confer male sterility.

Disease Resistance: Resistance to various diseases is evaluated and is expressed on a scale of 0=not tested, 1=resistant, 3=moderately resistant, 5=moderately susceptible, 7=susceptible, and 9=highly susceptible.

Erucic Acid Content: The percentage of the fatty acids in the form of C22:1. as determined by one of the methods recommended by the WCC/RRC, being AOCS Official Method Ce 2-66 Preparation of Methyl esters of Long-Chain Fatty Acids or AOCS Official Method Ce 1-66 Fatty Acid Composition by Gas Chromatography.

F1 Progeny. A first generation progeny plant produced by crossing a plant of canola variety S00616B1 with a plant of another canola plant.

Fatty Acid Content: The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length.

Flower Bud Location. A determination is made whether typical buds are disposed above or below the most recently opened flowers. Flower Date 50%. (Same as Time to Flowering) The number of days from planting until 50% of the plants in a planted area have at least one open flower.

Flower Petal Coloration. The coloration of open exposed petals on the first day of flowering is observed.

Frost Tolerance (Spring Type Only). The ability of young plants to withstand late spring frosts at a typical growing area is evaluated and is expressed on a scale of 1 (poor) to 5 (excellent).

Gene Silencing. The interruption or suppression of the expression of a gene at the level of transcription or translation.

Genotype. Refers to the genetic constitution of a cell or organism.

Glucosinolate Content. The total glucosinolates of seed at 8.5% moisture, as measured by AOCS Official Method AK-1-92 (determination of glucosinolates content in rapeseed—colza by HPLC), is expressed as micromoles per gram of defatted, oil-free meal. Capillary gas chromatography of the trimethylsityl derivatives of extracted and purified desulfoglucosinolates with optimization to obtain optimum indole glucosinolate detection is described in "Procedures of the Western Canada Canola/Rapeseed Recommending Committee Incorporated for the Evaluation and Recommendation for Registration of Canola/Rapeseed Candidate Cultivars in Western Canada". Also, glucosinolates could be analyzed using NIR (Near Infrared) spectroscopy as long as the instrument is calibrated according to the manufacturer's specifications.

Grain. Seed produced by the plant or a self or sib of the plant that is intended for food or feed use.

Green Seed. The number of seeds that are distinctly green throughout as defined by the Canadian Grain Commission. Expressed as a percentage of seeds tested.

Herbicide Resistance: Resistance to various herbicides when applied at standard recommended application rates is expressed on a scale of 1 (resistant), 2 (tolerant), or 3 (susceptible).

Leaf Anthocyanin Coloration. The presence or absence of leaf anthocyanin coloration, and the degree thereof if present, are observed when the plant has reached the 9- to 11-leaf stage.

Leaf Attachment to Stem. The presence or absence of clasping where the leaf attaches to the stem, and when present the degree thereof, are observed.

Leaf Attitude. The disposition of typical leaves with respect to the petiole is observed when at least 6 leaves of the plant are formed.

Leaf Color. The leaf blade coloration is observed when at least six leaves of the plant are completely developed.

Leaf Glaucosity or Waxiness. The presence or absence of a fine whitish powdery coating on the surface of the leaves, and the degree thereof when present, are observed.

Leaf Length. The length of the leaf blades and petioles are observed when at least six leaves of the plant are completely developed.

Leaf Lobes. The fully developed upper stem leaves are observed for the presence or absence of leaf lobes when at least 6 leaves of the plant are completely developed.

Leaf Margin Indentation. A rating of the depth of the indentations along the upper third of the margin of the largest leaf. 1=absent or very weak (very shallow), 3=weak (shallow), 5=medium, 7=strong (deep), 9=very strong (very deep).

Leaf Margin Hairiness. The leaf margins of the first leaf are observed for the presence or absence of pubescence, and the degree thereof, when the plant is at the two leaf-stage.

Leaf Margin Shape. A visual rating of the indentations along the upper third of the margin of the largest leaf. 1=undulating, 2=rounded, 3=sharp.

Leaf Surface or Texture. The leaf surface is observed for the presence or absence of wrinkles when at least six leaves of the plant are completely developed.

Leaf Tip Reflexion. The presence or absence of bending of typical leaf tips and the degree thereof, if present, are observed at the six to eleven leaf-stage.

Leaf Upper Side Hairiness. The upper surfaces of the leaves are observed for the presence or absence of hairiness, and the degree thereof if present, when at least six leaves of the plant are formed.

Leaf Width. The width of the leaf blades is observed when at least six leaves of the plant are completely developed.

Locus. A specific location on a chromosome.

Locus Conversion. A locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single canola variety.

Lodging Resistance. Resistance to lodging at maturity is observed. 1=not tested, 3=poor, 5=fair, 7=good, 9=excellent.

LSD. Abbreviation for least significant difference.

Maturity or Time to Maturity. The number of days from planting to maturity is observed, with maturity being defined as the plant stage when pods with seed change color, occurring from green to brown or black, on the bottom third of the pod-bearing area of the main stem.

NMS. Abbreviation for nuclear male sterility.

Number of Leaf Lobes. The frequency of leaf lobes, when present, is observed when at least six leaves of the plant are completely developed.

Oil Content: The typical percentage by weight oil present in the mature whole dried seeds is determined by ISO 10565:1993 Oilseeds Simultaneous determination of oil and water—Pulsed NMR method. Also, oil could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

Pedicel Length. The typical length of the silique stem when mature is observed. 3=short, 5=medium, 7=long.

Petal Length. The lengths of typical petals of fully opened flowers are observed. 3=short, 5=medium, 7=long.

Petal Spacing. Flower petal spacing is the measurement of how the petals are arranged in the flower. The petals should be observed when they are fully open, but not wilted. Spacing is rated on a scale of 1-9, 1 being thin petals with a large space between them, and 9 being large leaved with a strong overlap.

Petal Width. The widths of typical petals of fully opened flowers are observed. 3=short, 5=medium, 7=long.

Petiole Length. The length of the petioles is observed, in a line forming lobed leaves, when at least six leaves of the plant are completely developed. 3=short, 5=medium, 7=long.

Plant. As used herein, the term "plant" includes reference to an immature or mature whole plant, including a plant that has been emasculated or from which seed or grain has been removed. Seed or embryo that will produce the plant is also considered to be the plant.

Plant Part. As used herein, the term "plant part" includes leaves, stems, roots, seed, grain, embryo, pollen, ovules, flowers, husks, stalks, root tips, anthers, pericarp, tissue, cells and the like.

Plant Height. The overall plant height at the end of flowering is observed. 3=short, 5=medium, 7=tall.

Platform indicates the variety with the base genetics and the variety with the base genetics comprising locus conversion(s). There can be a platform for the inbred canola variety and the hybrid canola variety.

Ploidy. This refers to the number of chromosomes exhibited by the line, for example diploid or tetraploid.

Pod Anthocyanin Coloration. The presence or absence at maturity of silique anthocyanin coloration, and the degree thereof if present, are observed.

Pod (Silique) Beak Length. The typical length of the silique beak when mature is observed. 3=short, 5=medium, 7=long. Pod Habit. The typical manner in which the siliques are borne on the plant at maturity is observed.

Pod (Silique) Length. The typical silique length is observed. 1=short (less than 7 cm), 5=medium (7 to 10 cm), 9=long (greater than 10 cm).

Pod (Silique) Attitude or Angle. A visual rating of the angle joining the pedicel to the pod at maturity. 1=erect, 3=semi-erect, 5=horizontal, 7=semi-drooping, 9=drooping.

Pod Type. The overall configuration of the silique is observed.

Pod (Silique) Width. The typical pod width when mature is observed. 3=narrow (3 mm), 5=medium (4 mm), 7=wide (5 mm).

Pollen Formation. The relative level of pollen formation is observed at the time of dehiscence.

Protein Content: The typical percentage by weight of protein in the oil free meal of the mature whole dried seeds is determined by AOCS Official Method Ba 4e-93 Combustion Method for the Determination of Crude Protein. Also, protein could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

Resistance. The ability of a plant to withstand exposure to an insect, disease, herbicide, or other condition. A resistant plant variety or hybrid will have a level of resistance higher than a comparable wild-type variety or hybrid. "Tolerance" is a term commonly used in crops affected by *Sclerotinia*, and is used to describe an improved level of field resistance.

Root Anthocyanin Coloration. The presence or absence of anthocyanin coloration in the skin at the top of the root is observed when the plant has reached at least the six-leaf stage.

Root Anthocyanin Expression. When anthocyanin coloration is present in skin at the top of the root, it further is observed for the exhibition of a reddish or bluish cast within such coloration when the plant has reached at least the six-leaf stage.

Root Anthocyanin Streaking. When anthocyanin coloration is present in the skin at the top of the root, it further is observed for the presence or absence of streaking within such coloration when the plant has reached at least the six-leaf stage.

Root Chlorophyll Coloration. The presence or absence of chlorophyll coloration in the skin at the top of the root is observed when the plant has reached at least the six-leaf stage.

Root Coloration Below Ground. The coloration of the root skin below ground is observed when the plant has reached at least the six-leaf stage.

Root Depth in Soil. The typical root depth is observed when the plant has reached at least the six-leaf stage.

Root Flesh Coloration. The internal coloration of the root flesh is observed when the plant has reached at least the six-leaf stage.

SE. Abbreviation for standard error. Seedling Growth Habit. The growth habit of young seedlings is observed for the presence of a weak or strong rosette character. 1=weak rosette, 9=strong rosette.

Seeds Per Pod. The average number of seeds per pod is observed.

Seed Coat Color. The seed coat color of typical mature seeds is observed. 1=black, 2=brown, 3=tan, 4=yellow, 5=mixed, 6=other.

Seed Coat Mucilage. The presence or absence of mucilage on the seed coat is determined and is expressed on a scale of 1 (absent) to 9 (present). During such determination a petri dish is filled to a depth of 0.3 cm. with water provided at room temperature. Seeds are added to the petri dish and are immersed in water where they are allowed to stand for five minutes. The contents of the petri dish containing the immersed seeds are then examined under a stereo microscope equipped with transmitted light. The presence of mucilage and the level thereof is observed as the intensity of a halo surrounding each seed.

Seed Size or Seed Weight. The weight in grams of 1,000 typical seeds is determined at maturity while such seeds exhibit a moisture content of approximately 5 to 6 percent by weight.

Shatter Resistance. Resistance to silique shattering is observed at seed maturity. 1=not tested, 3=poor, 5=fair, 7=good, 9=does not shatter.

SI. Abbreviation for self-incompatible.

Speed of Root Formation. The typical speed of root formation is observed when the plant has reached the four to eleven-leaf stage.

SSFS. Abbreviation for *Sclerotinia sclerotiorum* Field Severity score, a rating based on both percentage infection and disease severity.

Stem Anthocyanin Intensity. The presence or absence of leaf anthocyanin coloration and the intensity thereof, if present, are observed when the plant has reached the nine to eleven-leaf stage. 1=absent or very weak, 3=weak, 5=medium, 7=strong, 9=very strong.

Stem Lodging at Maturity. A visual rating of a plant's ability to resist stem lodging at maturity. 1=very weak (lodged), 9=very strong (erect).

Time to Flowering. A determination is made of the number of days when at least 50 percent of the plants have one or more open buds on a terminal raceme in the year of sowing.

Seasonal Type. This refers to whether the new line is considered to be primarily a Spring or Winter type of canola.

Variety. A canola line and minor genetic modifications thereof that retain the overall genetics of the line including but not limited to a locus conversion, a cytoplasm conversion, a mutation, or a somoclonal variant.

Winter Survival (Winter Type Only). The ability to withstand winter temperatures at a typical growing area is evaluated and is expressed on a scale of 1 (poor) to 5 (excellent).

DETAILED DESCRIPTION

Field crops are bred through techniques that take advantage of the plant's method of pollination. A plant is self-pollinated if pollen from one flower is transferred to the same or another flower of the same plant or a genetically identical plant. A plant is sib-pollinated when individuals within the same family or line are used for pollination. A plant is cross-pollinated if the pollen comes from a flower on a genetically different plant from a different family or line. The term "cross-pollination" used herein does not include self-pollination or sib-pollination.

The breeder often initially selects and crosses two or more parental lines, followed by repeated selfing and selection, thereby producing many unique genetic combinations. In each cycle of evaluation, the plant breeder selects the germplasm to advance to the next generation. This germplasm is grown under chosen geographical, climatic, and soil conditions, and further selections are then made. The unpredictability of genetic combinations commonly results in the expenditure of large effort to develop a new and superior canola variety.

Canola breeding programs utilize techniques such as mass and recurrent selection, backcrossing, pedigree breeding and haploidy. Recurrent selection is used to improve populations of either self- or cross-pollinating *Brassica*. Through recurrent selection, a genetically variable population of heterozygous individuals is created by intercrossing several different parents. The best plants are selected based on individual superiority, outstanding progeny, and/or excellent combining ability. The selected plants are intercrossed to produce a new population in which further cycles of selection are continued. Various recurrent selection techniques are used to improve quantitatively inherited traits controlled by numerous genes.

Breeding programs use backcross breeding to transfer genes for a simply inherited, highly heritable trait into another line that serves as the recurrent parent. The source of the trait to be transferred is called the donor parent. After the initial cross, individual plants possessing the desired trait of the donor parent are selected and are crossed (back-crossed) to the recurrent parent for several generations. The resulting plant is expected to have the attributes of the recurrent parent and the desirable trait transferred from the donor parent. This approach has been used for breeding disease resistant phenotypes of many plant species, and has been used to transfer low erucic acid and low glucosinolate content into lines and breeding populations of Brassica.

Pedigree breeding and recurrent selection breeding methods are used to develop varieties from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding, five or more generations of selfing and selection are practiced: $F_1$ to $F_2$; $F_2$ to $F_3$; $F_3$ to $F_4$; $F_4$ to $F_5$, etc. For example, two parents that are believed to possess favorable complementary traits are crossed to produce an $F_1$. An $F_2$ population is produced by selfing one or several $F_1$'s or by intercrossing two $F_1$'s (i.e., sib mating). Selection of the best individuals may begin in the $F_2$ population, and beginning in the $F_3$ the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars. Backcrossing may be used in conjunction with pedigree breeding; for example, a combination of backcrossing and pedigree breeding with recurrent selection has been used to incorporate blackleg resistance into certain cultivars of Brassica napus.

Plants that have been self-pollinated and selected for type for many generations become homozygous at almost all gene loci and produce a uniform population of true breeding progeny. If desired, double-haploid methods can also be used to extract homogeneous lines from inbred G00555. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

The choice of breeding or selection methods depends on the mode of plant reproduction, the heritability of the trait(s) being improved, and the type of cultivar used commercially, such as $F_1$ hybrid variety or open pollinated variety. A true breeding homozygous line can also be used as a parental line (inbred line) in a commercial hybrid. If the line is being developed as an inbred for use in a hybrid, an appropriate pollination control system should be incorporated in the line. Suitability of an inbred line in a hybrid combination will depend upon the combining ability (general combining ability or specific combining ability) of the inbred.

Various breeding procedures can be utilized with these breeding and selection methods and inbred G00555. The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, one or more pods from each plant in a population are threshed together to form a bulk. Part of the bulk is used to plant the next generation and part is put in reserve. The procedure has been referred to as modified single-seed descent or the pod-bulk technique. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed. If desired, doubled-haploid methods can be used to extract homogeneous lines.

Molecular markers, including techniques such as Isozyme Electrophoresis, Restriction Fragment Length Polymorphisms (RFLP), random amplified polymorphic DNA (RAPD), amplified fragment length polymorphism (AFLP), inter-simple sequence repeats (ISSRs), sequence characterized regions (SCARs), sequence tag sites (STSs), cleaved amplified polymorphic sequences (CAPS), microsatellites, simple sequence repeats (SSRs), expressed sequence tags (ESTs), single nucleotide polymorphisms (SNPs), and diversity arrays technology (DArT), sequencing, and the like may be used in plant breeding methods using G00555. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles in the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection or Marker Assisted Selection (MAS). p Methods of isolating nucleic acids from G00555 and methods for performing genetic marker profiles using SNP and SSR polymorphisms are provided. SNPs are genetic markers based on a polymorphism in a single nucleotide. A marker system based on SNPs can be highly informative in linkage analysis relative to other marker systems in that multiple alleles may be present.

A method comprising isolating nucleic acids, such as DNA, from a plant, a plant part, plant cell or a seed of the canola varieties disclosed herein is provided. The method can include mechanical, electrical and/or chemical disruption of the plant, plant part, plant cell or seed, contacting the disrupted plant, plant part, plant cell or seed with a buffer or solvent, to produce a solution or suspension comprising nucleic acids, optionally contacting the nucleic acids with a precipitating agent to precipitate the nucleic acids, optionally extracting the nucleic acids, and optionally separating the nucleic acids such as by centrifugation or by binding to beads or a column, with subsequent elution, or a combination thereof. If DNA is being isolated, an RNase can be included in one or more of the method steps. The nucleic acids isolated can comprise all or substantially all of the genomic DNA sequence, all or substantially all of the chromosomal DNA sequence or all or substantially all of the coding sequences (cDNA) of the plant, plant part, or plant cell from which they were isolated. The nucleic acids isolated can comprise all, substantially all, or essentially all of the genetic complement of the plant. The nucleic acids isolated can comprise a genetic complement of the canola variety. The amount and type of nucleic acids isolated may be sufficient to permit whole genome sequencing of the plant from which they were isolated or chromosomal marker analysis of the plant from which they were isolated.

The methods can be used to produce nucleic acids from the plant, plant part, seed or cell, which nucleic acids can be, for example, analyzed to produce data. The data can be recorded. The nucleic acids from the disrupted cell, the disrupted plant, plant part, plant cell or seed or the nucleic acids following isolation or separation can be contacted with primers and nucleotide bases, and/or a polymerase to facilitate PCR sequencing or marker analysis of the nucleic acids. In some examples, the nucleic acids produced can be sequenced or contacted with markers to produce a genetic profile, a molecular profile, a marker profile, a haplotype, or any combination thereof. In some examples, the genetic profile or nucleotide sequence is recorded on a computer readable medium. In other examples, the methods may further comprise using the nucleic acids produced from plants, plant parts, plant cells or seeds in a plant breeding program, for example in making crosses, selection and/or advancement decisions in a breeding program. Crossing includes any type of plant breeding crossing method, including but not limited to crosses to produce hybrids, outcrossing, selfing, backcrossing, locus conversion, introgression and the like. Favorable genotypes and or marker profiles, optionally associated with a trait of interest, may be identified by one or more methodologies. In some examples one or more markers are used, including but not limited to restriction fragment length polymorphism (RFLP), random amplified polymorphic DNA (RAPD), amplified fragment length polymorphism (AFLP), inter-simple sequence repeats (ISSRs), sequence characterized regions (SCARs), sequence tag sites (STSs), cleaved amplified polymorphic sequences (CAPS), microsatellites, simple sequence repeats (SSRs), expressed sequence tags (ESTs), single nucleotide polymorphisms (SNPs), and diversity arrays technology (DArT), sequencing, and the like. In some methods, a target nucleic acid is amplified prior to hybridization with a probe. In other cases, the target nucleic acid is not amplified prior to hybridization, such as methods using molecular inversion probes. In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis. G00555 and its plant parts can be identified through a molecular marker profile. Such plant parts may be either diploid or haploid. Also encompassed and described are plants and plant parts substantially benefiting from the use of variety G00555 in their development, such as variety G00555 comprising a locus conversion or single locus conversion.

The production of doubled haploids can also be used for the development of inbreds from G00555 in a breeding program. In *Brassica napus*, microspore culture technique is used in producing haploid embryos. The haploid embryos are then regenerated on appropriate media as haploid plantlets, doubling chromosomes of which results in doubled haploid plants. This can be advantageous because the process omits the generations of selfing needed to obtain a homozygous plant from a heterozygous source.

Controlling Self-Pollination

Canola varieties are mainly self-pollinated. A pollination control system and effective transfer of pollen from one parent to the other provides an effective method for producing hybrid canola seed and plants. For example, the ogura cytoplasmic male sterility (CMS) system, developed via protoplast fusion between radish (*Raphanus sativus*) and rapeseed (*Brassica napus*), is one of the most frequently used methods of hybrid production. It provides stable expression of the male sterility trait and an effective nuclear restorer gene. The OGU INRA restorer gene, Rf1 originating from radish has improved versions.

*Brassica* hybrid varieties can be developed using self-incompatible (SI), cytoplasmic male sterile (CMS) or nuclear male sterile (NMS) *Brassica* plants as the female parent such that only cross pollination will occur between the hybrid parents.

In one instance, production of $F_1$ hybrids includes crossing a CMS *Brassica* female parent with a pollen-producing male *Brassica* has a fertility restorer gene (Rf gene). The presence of an Rf gene means that the $F_1$ generation will not be completely or partially sterile, so that either self-pollination or cross pollination may occur. Self pollination of the $F_1$ generation to produce several subsequent generations verifies that a desired trait is heritable and stable and that a new variety has been isolated.

Other sources and refinements of CMS sterility in canola include the Polima cytoplasmic male sterile plant, as well as those of U.S. Pat. No. 5,789,566, DNA sequence imparting cytoplasmic male sterility, mitochondrial genome, nuclear genome, mitochondria and plant containing said sequence and process for the preparation of hybrids; See U.S. Pat. Nos. 4,658,085, 5,973,233 and 6,229,072.

Hybrid Development

For many traits the true genotypic value may be masked by other confounding plant traits or environmental factors.

One method for identifying a superior plant is to observe its performance relative to other experimental plants and to one or more widely grown standard varieties. If a single observation is inconclusive, replicated observations provide a better estimate of the genetic worth.

As a result of the advances in sterility systems, lines are developed that can be used as an open pollinated variety (i.e., a pureline cultivar) and/or as a sterile inbred (female) used in the production of $F_1$ hybrid seed. In the latter case, favorable combining ability with a restorer (male) would be desirable.

The development of a canola hybrid generally involves three steps: (1) the selection of plants from various germplasm pools for initial breeding crosses; (2) generation of inbred lines, such as by selfing of selected plants from the breeding crosses for several generations to produce a series of different inbred lines, which breed true and are highly uniform; and (3) crossing the selected inbred lines with different inbred lines to produce the hybrids.

Combining ability of a line, as well as the performance of the line per se, is a factor in the selection of improved canola lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

*Brassica napus* canola plants, absent the use of sterility systems, are recognized to commonly be self-fertile with approximately 70 to 90 percent of the seed normally forming as the result of self-pollination. The percentage of cross pollination may be further enhanced when populations of recognized insect pollinators at a given growing site are greater. Thus open pollination is often used in commercial canola production.

Locus Conversions of Canola Variety G00555

G00555 represents a new base genetic line into which a new locus or trait may be introduced. Direct transformation, genetic editing or gene modification such as described herein and backcrossing can be used to accomplish such an introgression. The term locus conversion is used to designate the product of such an introgression. Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of G00555 may be characterized as having essentially the same phenotypic traits as G00555 or otherwise all of the physiological and morphological characteristics of G00555. The traits used for comparison may be those traits shown in Table 1. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

A locus conversion of G00555 may contain at least 1, 2, 3, 4 or 5 locus conversions, and fewer than 15, 10, 9, 8, 7, or 6 locus conversions. A locus conversion of G00555 will otherwise retain the genetic integrity of G00555. For example, a locus conversion of G00555 can be developed when DNA sequences are introduced through backcrossing, with a parent of G00555 utilized as the recurrent parent. Both naturally occurring and transgenic DNA sequences may be introduced through backcrossing techniques. A backcross conversion may produce a plant with a locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, a backcross conversion can be made in as few as two backcrosses. A locus conversion of G00555 can be determined through the use of a molecular profile. A locus conversion of G00555 may have at least 92%, 93%, 94%, 95%, 96%, 97%, 98% or 99% of the molecular markers, or molecular profile, of G00555. Examples of molecular markers that could be used to determine the molecular profile include RFLP, PCR analysis, SSR and SNPs.

Examples of locus conversions or transgenes which may be using include one or more that confer male sterility, a site for site-specific recombination, abiotic stress tolerance, altered phosphate content, altered antioxidants, altered fatty acid content, altered essential amino acid content, altered carbohydrate content, herbicide resistance, insect resistance, disease resistance or a combination thereof. Other desirable traits which may be modified include tolerance to heat and drought, reducing the time to crop maturity, greater yield, and better agronomic quality, increased amount or rate of germination, stand establishment, growth rate, maturity, and plant and pod height.

Disease—*Sclerotinia*

*Sclerotinia* infects over 100 species of plants, including *Brassica* species. *Sclerotinia sclerotiorum* is responsible for over 99% of *Sclerotinia* disease, while *Sclerotinia minor* produces less than 1% of the disease. *Sclerotinia* produces sclerotia, irregularly-shaped, dark overwintering bodies, which can endure in soil for four to five years. The sclerotia can germinate carpogenically or myceliogenically, depending on the environmental conditions and crop canopies. The two types of germination cause two distinct types of diseases. Sclerotia that germinate carpogenically produce apothecia and ascospores that infect above-ground tissues, resulting in stem blight, stalk rot, head rot, pod rot, white mold and blossom blight of plants. Sclerotia that germinate myceliogenically produce mycelia that infect root tissues, causing crown rot, root rot and basal stalk rot.

*Sclerotinia* causes *Sclerotinia* stem rot, also known as white mold, in *Brassica*, including canola. The disease is favored by moist soil conditions (at least 10 days at or near field capacity) and temperatures of 15-25° C., prior to and during canola flowering. The spores cannot infect leaves and stems directly; they must first land on flowers, fallen petals, and pollen on the stems and leaves. The fungal spores use the flower parts as a food source as they germinate and infect the plant.

The severity of *Sclerotinia* in *Brassica* is variable, and is dependent on the time of infection and climatic conditions, being favored by cool temperatures between 20 and 25° C., prolonged precipitation and relative humidities of greater than 80%. Losses ranging from 5 to 100% have been reported for individual fields. *Sclerotinia* can cause heavy losses in wet swaths and result in economic losses of millions of dollars.

The symptoms of *Sclerotinia* infection usually develop several weeks after flowering begins. The infections often develop where the leaf and the stem join. Infected stems appear bleached and tend to shred. Hard black fungal sclerotia develop within the infected stems, branches, or pods. Plants infected at flowering produce little or no seed. Plants with girdled stems wilt and ripen prematurely. Severely infected crops frequently lodge, shatter at swathing, and make swathing more time consuming. Infections can occur in all above-ground plant parts, especially in dense or lodged stands, where plant-to-plant contact facilitates the spread of infection. New sclerotia carry the disease over to the next season.

Conventional methods for control of *Sclerotinia* diseases include (a) chemical control (fungicides such as benomyl, vinclozolin, iprodione, azoxystrobin, prothioconazole, boscalid), (b) disease resistance (such as partial resistance and breeding for favorable morphologies such as increased standability, reduced petal retention, branching (less compact and/or higher), and early leaf abscission) and (c) cultural control.

Methods for generating *Sclerotinia* resistant *Brassica* plants using inbred line G00555 are provided, including crossing with one or more lines containing one or more genes contributing to *Sclerotinia* resistance and selecting for resistance. In some embodiments, G00555 can be modified to have resistance to *Sclerotinia*.

The inbred line G00555 can be used in breeding techniques to create canola hybrids. For example, inbred line G00555 may be used as a female parent, male parent or restorer (R-line), A-line, maintainer (B-line) in a canola hybrid.

An OGU restorer version, or R-line, of variety G00555 is provided which is a male line that carries a gene for the restoration of fertility. When a sterile CMS version of an inbred is pollinated by a male line that carries a gene for the restoration of fertility, it results in a fertile hybrid. Generally, the seed produced from this cross is the seed that is commercially sold.

There are a number of analytical methods available to determine the phenotypic stability of a canola variety. Phenotypic trait data are usually collected in field experiments including for example traits associated with seed yield, seed oil content, seed protein content, fatty acid composition of oil, glucosinolate content of meal, growth habit, lodging resistance, plant height, shattering resistance, etc.

In addition to phenotypic observations, the genotype of a plant can also be examined. A plant's genotype can be used to identify plants of the same variety or a related variety, or pedigree. Genotyping techniques include Isozyme Electrophoresis, RFLPs, RAPDs, AP-PCR, DAF, SCARs, AFLPs, SSRs which are also referred to as Microsatellites and SNPs.

The variety described herein has shown uniformity and stability for all traits, such as described in Table 1. When preparing the detailed phenotypic information, plants of variety G00555 were observed while being grown using conventional agronomic practices.

Variety G00555 can be advantageously used in accordance with the breeding methods described herein and those known in the art to produce hybrids and other progeny plants retaining desired trait combinations of G00555. Provided are methods for producing a canola plant by crossing a first parent canola plant with a second parent canola plant wherein either the first or second parent canola plant is canola variety G00555. Further, both first and second parent canola plants can come from the canola variety G00555. Either the first or the second parent plant may be male sterile.

Still further, methods to produce a G00555-derived canola plant are provided by crossing canola variety G00555 with a second canola plant and growing the progeny seed, and repeating the crossing and growing steps with the canola G00555-derived plant at least 1, 2 or 3 times and less than 7, 6, 5, 4, 3 or 2 times. Any such methods using the canola variety G00555 may include one or more of open pollination, selfing, backcrosses, hybrid production, crosses to populations, and the like. All plants produced using canola variety G00555 as a parent, including plants derived from canola variety G00555 are provided herein. Plants derived or produced from G00555 may include components for either male sterility or for restoration of fertility. Advantageously, the canola variety is used in crosses with other, different, canola plants to produce first generation ($F_1$) canola hybrid seeds and plants with superior characteristics.

A single-gene or a single locus conversion of G00555 is provided. Single-gene conversions and single locus conversions can occur when DNA sequences are introduced through traditional (non-transformation) breeding techniques, such as backcrossing. DNA sequences, whether naturally occurring, modified or transgenes, may be introduced using these traditional breeding techniques. Desired traits transferred through this process include, but are not limited to, fertility restoration, fatty acid profile modification, oil content modification, protein quality or quantity modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single-gene traits may result from the transfer of either a dominant allele or a recessive allele. Selection of progeny containing the trait of interest is done by direct selection for a trait associated with a dominant allele. Selection of progeny for a trait that is transferred via a recessive allele will require growing and selfing the first backcross to determine which plants carry the recessive alleles. Recessive traits may require additional progeny testing in successive backcross generations to determine the presence of the gene of interest.

It should be understood that the canola variety described herein can, through routine manipulation by cytoplasmic genes, nuclear genes, or other factors, be produced in a male-sterile or restorer form as described in the references discussed earlier. Canola variety G00555 can be manipulated to be male sterile by any of a number of methods known in the art, including by the use of mechanical methods, chemical methods, SI, CMS (either ogura or another system) or NMS. The term "manipulated to be male sterile" refers to the use of any available techniques to produce a male sterile version of canola variety G00555. The male sterility may be either partial or complete male sterility. F1 hybrid seed and plants produced by the use of canola variety G00555 are provided. Canola variety G00555 can also further comprise a component for fertility restoration of a male sterile plant, such as an Rf restorer gene. In this case, canola variety G00555 could then be used as the male plant in hybrid seed production.

G00555 can be used in tissue culture. As used herein, the term plant includes plant protoplasts, plant cell tissue cultures from which canola plants can be regenerated, plant calli, plant clumps, and plant cells that are intact in plants or parts of plants, such as embryos, pollen, ovules, seeds, flowers, leaves, husks, stalks, roots, root tips, anthers and the like. Tissue culture and microspore cultures and the regeneration of canola plants therefrom are provided.

The utility of canola variety G00555 also extends to crosses with other species than just *Brassica napus*. Commonly, suitable species will be of the family Brassicae.

Molecular biological techniques allow the isolation and characterization of genetic elements with specific functions, such as encoding specific protein products. The genome of plants can be engineered to contain and express foreign genetic elements, or additional or modified versions of native or endogenous genetic elements in order to alter the traits of a plant in a specific manner. Any DNA sequences, whether from a different species or from the same species, that are inserted into the genome using transformation are referred to herein collectively as "transgenes". Gene editing can insert, delete or substitute native polynucleotide sequences to produce increased or decreased expression or activity of a polypeptide of interest. Described herein are transformed and edited versions of the claimed canola variety G00555.

Numerous methods for plant transformation have been developed, including biological and physical plant transformation protocols. In addition, expression vectors and in vitro culture methods for plant cell or tissue transformation and regeneration of plants are available. The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

In general, methods to transform, modify, edit or alter plant endogenous genomic DNA include altering the plant native DNA sequence or introducing a pre-existing transgenic sequence including regulatory elements, coding and non-coding sequences. Genetic transformation methods include introduction of foreign or heterologous sequences and genome editing techniques which modify the native sequence. Transformation methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1).

A genetic trait which has been engineered into a particular canola plant using transformation and/or gene editing techniques, could be moved into another line using traditional breeding techniques that are well known in the plant breeding arts. For example, a backcrossing approach could be used to move a transgene or modified gene from a transformed or modified canola plant to an elite inbred line and the resulting progeny would comprise a transgene or modified gene. Also, if an inbred line was used for the transformation or genetic modification then the transgenic or modified plants could be crossed to a different line in order to produce a transgenic or modified hybrid canola plant. As used herein, "crossing" can refer to a simple X by Y cross, or the process of backcrossing, depending on the context. Various genetic elements can be introduced into the plant genome using transformation or gene editing. These elements include but are not limited to genes; coding sequences; inducible, constitutive, and tissue specific promoters; enhancing sequences; and signal and targeting sequences.

Transgenic and modified plants described herein can produce a foreign or modified protein in commercial quantities. Thus, techniques for the selection and propagation of transformed plants, which are well understood in the art, may yield a plurality of transgenic or modified plants which are harvested in a conventional manner, and a foreign or modified protein then can be extracted from a tissue of interest or from total biomass.

A genetic map can be generated, for example via conventional RFLP, PCR analysis, SSR and SNPs, which identifies the approximate chromosomal location of the integrated DNA molecule coding for the foreign protein. Genetic or physical map information concerning chromosomal location is useful for proprietary protection of a subject transgenic or modified plant. If unauthorized propagation is undertaken and crosses made with other germplasm, the map of the integration or modified region can be compared to similar maps for suspect plants, to determine if the latter have a common parentage with the subject plant. Map comparisons would involve hybridizations, RFLP, PCR, SSR, SNP, and sequencing, all of which are conventional techniques.

Likewise, disclosed are plants genetically engineered or modified to express various phenotypes of agronomic interest. Exemplary transgenes or modified genes implicated in this regard include, but are not limited to, those categorized below.

1. Genes that confer resistance to pests or disease and that encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. A plant resistant to a disease is one that is more resistant to a pathogen as compared to the wild type plant.

(B) A gene conferring resistance to fungal pathogens.

(C) A *Bacillus thuringiensis* protein, a derivative thereof or a synthetic polypeptide modeled thereon. DNA molecules encoding delta-endotoxin genes can be purchased from American Type Culture Collection (Manassas, Va.), for example, under ATCC Accession Nos. 40098, 67136, 31995 and 31998. Other examples of *Bacillus thuringiensis* transgenes are given in the following US and international patents and applications: U.S. Pat. Nos. 5,188,960; 5,689,052; 5,880,275; WO 91/114778; WO 99/31248; WO 01/12731; WO 99/24581; WO 97/40162.

(D) An insect-specific hormone or pheromone such as an ecdysteroid and juvenile hormone, a variant thereof, a mimetic based thereon, or an antagonist or agonist thereof.

(E) An insect-specific peptide which, upon expression, disrupts the physiology of the affected pest. For example, DNA coding for insect diuretic hormone receptor, allostatins and genes encoding insect-specific, paralytic neurotoxins.

(F) An enzyme responsible for a hyperaccumulation of a monterpene, a sesquiterpene, a steroid, hydroxamic acid, a phenylpropanoid derivative or another non-protein molecule with insecticidal activity.

(G) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application No. WO 93/02197, which discloses the nucleotide sequence of a callase gene. DNA molecules which contain chitinase-encoding sequences can be obtained, for example, from the ATCC under Accession Nos. 39637 and 67152. See also U.S. Pat. No. 6,563,020.

(H) A molecule that stimulates signal transduction. For example, nucleotide sequences encoding calmodulin.

(I) A hydrophobic moment peptide. See, U.S. Pat. Nos. 5,580,852 and 5,607,914.

(J) A membrane permease, a channel former or a channel blocker. For example, a cecropin-beta lytic peptide analog.

(K) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

(L) An insect-specific antibody or an immunotoxin derived therefrom. Thus, an antibody targeted to a critical metabolic function in the insect gut would inactivate an affected enzyme, killing the insect.

(M) A virus-specific antibody. For example, transgenic plants expressing recombinant antibody genes can be protected from virus attack.

(N) A developmental-arrestive protein produced in nature by a pathogen or a parasite; for example, fungal endo alpha-1,4-D-polygalacturonases.

(O) A developmental-arrestive protein produced in nature by a plant.

(P) Genes involved in the Systemic Acquired Resistance (SAR) Response and/or the pathogenesis related genes.

(Q) Antifungal genes.

(R) Detoxification genes, such as for fumonisin, beauvericin, moniliformin and zearalenone and their structurally related derivatives. For example, see, U.S. Pat. No. 5,792,931.

(S) Cystatin and cysteine proteinase inhibitors. E.g., U.S. Pat. No. 7,205,453.

(T) Defensin genes.

(U) Genes that confer resistance to Phytophthora Root Rot, such as the *Brassica* equivalents of the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes.

2. Genes that confer resistance to an herbicide, for example:

(A) A herbicide that inhibits the growing point or meristem, such as an imidazalinone or a sulfonylurea. Exemplary genes in this category code for mutant ALS and AHAS enzyme. See also, U.S. Pat. Nos. 5,605,011; 5,013,659; 5,141,870; 5,767,361; 5,731,180; 5,304,732; 4,761,373; 5,331,107; 5,928,937 and 5,378,824.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835, which discloses the nucleotide sequence of a form of EPSP which can confer glyphosate resistance. See also, U.S. Pat. No. 7,405,074, and related applications, which disclose compositions and means for providing glyphosate resistance. U.S. Pat. No. 5,627,061 describes genes encoding EPSPS enzymes. See also, U.S. Pat. Nos. 6,566,587; 6,338,961; 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; Re. 36,449; RE 37,287 E; and U.S. Pat. No. 5,491,288; and international publications EP1173580; WO 01/66704; EP1173581 and EP1173582. A DNA molecule encoding a mutant aroA gene can be obtained under ATCC Accession No. 39256, see U.S. Pat. No. 4,769,061. European Patent Application No. 0 333 033, and U.S. Pat. No. 4,975,374 disclose nucleotide sequences of glutamine synthetase genes which confer resistance to herbicides such as L-phosphinothricin. The nucleotide sequence of a phosphinothricin-acetyl-transferase gene is provided in European Application No. 0 242 246. See also, U.S. Pat. Nos. 5,969,213; 5,489,520; 5,550,318; 5,874,265; 5,919,675; 5,561,236; 5,648,477; 5,646,024; 6,177,616 and 5,879,903. Exemplary of genes conferring resistance to phenoxy propionic acids and cycloshexones, such as sethoxydim and haloxyfop, are the Acc1-S1, Acc1-S2 and Acc1-S3 genes. See also, U.S. Pat. Nos. 5,188,642; 5,352,605; 5,530,196; 5,633,435; 5,717,084; 5,728,925; 5,804,425 and Canadian Patent No. 1,313,830.

(C) A herbicide that inhibits photosynthesis, such as a triazine (psbA and gs+genes) and a benzonitrile (nitrilase gene). Nucleotide sequences for nitrilase genes are disclosed in U.S. Pat. No. 4,810,648, and DNA molecules containing these genes are available under ATCC Accession Nos. 53435, 67441 and 67442.

(D) Acetohydroxy acid synthase, which has been found to make plants that express this enzyme resistant to multiple types of herbicides, has been introduced into a variety of plants. Other genes that confer tolerance to herbicides include: a gene encoding a chimeric protein of rat cytochrome P4507A1 and yeast NADPH-cytochrome P450 oxidoreductase, genes for glutathione reductase and superoxide dismutase, and genes for various phosphotransferases.

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; and 5,767,373; and international publication WO 01/12825.

3. Transgenes that confer or contribute to an altered grain characteristic, such as:
  (A) Altered fatty acids, for example, by
  (1) Down-regulation of stearoyl-ACP desaturase to increase stearic acid content of the plant. See, WO99/64579,
  (2) Elevating oleic acid via FAD-2 gene modification and/or decreasing linolenic acid via FAD-3 gene modification, See, U.S. Pat. Nos. 6,063,947; 6,323,392; 6,372,965 and WO 93/11245,
  (3) Altering conjugated linolenic or linoleic acid content, such as in WO 01/12800,
  (4) Altering LEC1, AGP, Dek1, Superalt milps, various Ipa genes such as Ipal, Ipa3, hpt or hggt. For example, see WO 02/42424, WO 98/22604, WO 03/011015, U.S. Pat. Nos. 6,423,886, 6,197,561, 6,825,397, US Patent Application Publication Nos. 2003/0079247, 2003/0204870, WO02/057439, WO03/011015.
  (B) Altered phosphorus content, for example, by the
  (1) Introduction of a phytase-encoding gene would enhance breakdown of phytate, adding more free phosphate to the transformed plant, such as for example, using an *Aspergillus niger* phytase gene.
  (2) Up-regulation of a gene that reduces phytate content.
  (C) Altered carbohydrates effected, for example, by altering a gene for an enzyme that affects the branching pattern of starch, a gene altering thioredoxin. (See, U.S. Pat. No. 6,531,648). Exemplary genes include those encoding fructosyltransferase, levansucrase, alpha-amylase, invertase, branching enzyme II, UDP-D-xylose 4-epimerase, Fragile 1 and 2, Ref1, HCHL (4-hydroxycinnamoyl-CoA hydratase/lyase), C4H (cinnamate 4-hydroxylase), AGP (ADPglucose pyrophosphorylase). The fatty acid modification genes may also be used to affect starch content and/or composition through the interrelationship of the starch and oil pathways.
  (D) Altered antioxidant content or composition, such as alteration of tocopherol or tocotrienols. For example, see, U.S. Pat. No. 6,787,683, US Patent Application Publication No. 2004/0034886 and WO 00/68393 involving the manipulation of antioxidant levels through alteration of a phytl prenyl transferase (ppt), WO 03/082899 through alteration of a homogentisate geranyl geranyl transferase (hggt).
  (E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication No. 2003/0163838, US Patent Application Publication No. 2003/0150014, US Patent Application Publication No. 2004/0068767, U.S. Pat. No. 6,803,498, WO01/79516, and WO00/09706 (Ces A: cellulose synthase), U.S. Pat. No. 6,194,638 (hem icellulose), U.S. Pat. No. 6,399,859 and US Patent Application Publication No. 2004/0025203 (UDPGdH), U.S. Pat. No. 6,194,638 (RGP).

4. Genes that control pollination, hybrid seed production or male-sterility:
  There are several methods of conferring genetic male sterility available, such as multiple mutant genes at separate locations within the genome that confer male sterility, as disclosed in U.S. Pat. Nos. 4,654,465 and 4,727,219 and chromosomal translocations, see U.S. Pat. Nos. 3,861,709 and 3,710,511. U.S. Pat. No. 5,432,068 describes a system of nuclear male sterility which includes replacing the native promoter of an essential male fertility gene with an inducible promoter to create a male sterile plant that can have fertility restored by inducing or turning "on", the promoter such that the male fertility gene is transcribed.
  (A) Introduction of a deacetylase gene under the control of a tapetum-specific promoter and with the application of the chemical N-Ac-PPT (WO 01/29237).
  (B) Introduction of various stamen-specific promoters (WO 92/13956, WO 92/13957).
  (C) Introduction of the barnase and the barstar gene.
  For additional examples of nuclear male and female sterility systems and genes, see also, U.S. Pat. Nos. 5,859,341; 6,297,426; 5,478,369; 5,824,524; 5,850,014 and 6,265,640.
  Also see, U.S. Pat. No. 5,426,041 (relating to a method for the preparation of a seed of a plant comprising crossing a male sterile plant and a second plant which is male fertile), U.S. Pat. No. 6,013,859 (molecular methods of hybrid seed production) and U.S. Pat. No. 6,037,523 (use of male tissue-preferred regulatory region in mediating fertility).

5. Genes that create a site for site specific DNA integration.
  This includes the introduction of FRT sites that may be used in the FLP/FRT system and/or Lox sites that may be used in the Cre/Loxp system. Other systems that may be used include the Gin recombinase of phage Mu, the Pin recombinase of *E. coli*, and the R/RS system of the pSR1 plasmid.

6. Genes that affect abiotic stress resistance (including but not limited to flowering and seed development, enhancement of nitrogen utilization efficiency, altered nitrogen responsiveness, drought resistance or tolerance, cold resistance or tolerance, and salt resistance or tolerance) and increased yield under stress.
  For example, see, U.S. Pat. Nos. 5,892,009, 5,965,705, 5,929,305, 5,891,859, 6,417,428, 6,664,446, 6,706,866, 6,717,034, 6,801,104. CBF genes and transcription factors effective in mitigating the negative effects of freezing, high salinity, and drought on plants can be used. Altering abscisic acid in plants may result in increased yield and/or increased tolerance to abiotic stress. Modifying cytokinin expression may result in plants with increased drought tolerance, and/or increased yield. Enhancement of nitrogen utilization and altered nitrogen responsiveness can be carried out. Ethylene alteration, plant transcription factors or transcriptional regulators of abiotic stress may be used. Other genes and transcription factors that affect plant growth and agronomic traits such as yield, flowering, plant growth and/or plant structure, can be introduced or introgressed into plants.

Seed Treatments and Cleaning

Methods of harvesting the seed of the canola variety G00555 as seed for planting are provided. Embodiments include cleaning the seed, treating the seed, and/or conditioning the seed. Cleaning the seed is understood in the art to include removal of foreign debris such as one or more of weed seed, chaff, and plant matter, from the seed. Conditioning the seed is understood in the art to include controlling the temperature and rate of dry down of the seed and storing seed in a controlled temperature environment. Seed treatment is the application of a composition to the surface of the seed such as a coating or powder. Methods for producing a treated seed include the step of applying a composition to the seed or seed surface. Seeds are provided which have on the surface a composition. Biological active components such as bacteria can also be used as a seed treatment. Some examples of compositions are insecticides, fungicides, pesticides, antimicrobials, germination inhibitors, germination promoters, cytokinins, and nutrients.

Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB (EPA registration number 00293500419, containing quintozen and terrazole), penflufen, penicillium, penthiopyrad, permethrine, picoxystrobin, prothioconazole, pyraclostrobin, rynaxypyr, S-metolachlor, saponin, sedaxane, TCMTB (2-(thiocyanomethylthio) benzothiazole), tebuconazole, thiabendazole, thiamethoxam, thiocarb, thiram, tolclofos-methyl, triadimenol, trichoderma, trifloxystrobin, triticonazole and/or zinc.

INDUSTRIAL APPLICABILITY

The seed of the G00555 variety or grain produced on its hybrids, plants produced from such seed, and various parts of the G00555 variety canola plant or its progeny can be utilized in the production of an edible vegetable oil, meal, other food products or silage for animal feed in accordance with known techniques. The oil as removed from the seeds can be used in food applications such as a salad or frying oil. Canola oil has low levels of saturated fatty acids. "Canola" refers to rapeseed (*Brassica*) which (1) has an erucic acid (C22:1) content of at most 2% (preferably at most 0.5% or 0%) by weight based on the total fatty acid content of a seed, and (2) produces, after crushing, an air-dried meal containing less than 30 μmol glucosinolates per gram of defatted (oil-free) meal. The oil also finds utility in industrial applications. The solid meal component derived from seeds after oil extraction can be used as a nutritious livestock feed. Examples of canola grain as a commodity plant product include, but are not limited to, oils and fats, meals and protein, and carbohydrates. Methods of processing seeds and grain of G00555 or of a hybrid and grain produced on the hybrid to produce commodity products such as oil and protein meal are provided.

All publications, patents, and patent applications mentioned in the specification are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

Deposits

Applicant has made a deposit of at least 625 seeds of canola line G00555 with the American Type Culture Collection (ATCC), Manassas, Va. 20110 USA, ATCC Deposit Number PTA-126282. The seeds deposited with the ATCC on Oct. 15, 2019 were taken from the deposit maintained by Pioneer Hi-Bred International, Inc., 7100 NW $62^{nd}$ Avenue, Johnston, Iowa 50131-1000 since prior to the filing date of this application. During the pendency of the application, access to this deposit will be available to the Commissioner of Patents and Trademarks and persons determined by the Commissioner to be entitled thereto upon request. Upon issuance of any claims in the application, the Applicant will make the deposit available to the public, pursuant to 37 CFR 1.808. This deposit of Canola line G00555 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have or will satisfy all the requirements of 37 C.F.R. §§ 1.801-1.809, including providing an indication of the viability of the sample. Applicant(s) have no authority to waive any restrictions imposed by law on the transfer of biological material or its transportation in commerce. Applicant(s) do not waive any infringement of their rights granted under this patent or under the Plant Variety Protection Act (7 USC 2321 et seq.).

Breeding History

G00555 was developed from a two way cross NS6569 with a proprietary line not disclosed to the public. NS6569 is described in U.S. Pat. No. 9,179,634. A doubled haploid population was created from this cross. The double-haploid lines were evaluated in a nursery for two years for general vigor, uniformity, maturity, oil, protein, total glucosinolates. Selected DH lines were used in testcross (hybrid) seed production using a common CMS female tester. The testcross hybrids were evaluated in preliminary trials at six locations. Based on testcross hybrid data, line G00555 was selected. Pure seed increase and production of G00555 line was conducted in subsequent years.

TABLE 1

Table 1. Variety Descriptions based on Morphological, Agronomic and Quality Traits
Morphological and Other Characteristics of Canola *Brassica napus* G00555

| Characteristic | Value |
|---|---|
| BEFORE FLOWERING | |
| Cotyledon Width (3 = Narrow, 5 = Medium, 7 = Wide) | 4 |
| Seedling Growth Habit (1 = Weak Rosette, 9 = Strong Rosette) | 5 |
| Stem Anthocyanin Intensity (1 = Absent or Very Weak, 3 = Weak, 5 = Medium, 7 = Strong, 9 = Very Strong) | 1 |
| Leaf Type (1 = Petiolate, 9 = Lyrate) | |
| Leaf Shape (3 = Narrow elliptic, 5 = Wide elliptic, 7 = Orbicular) | |
| Leaf Length (3 = Short, 5 = Medium, 7 = Long) | 3 |
| Leaf Width (3 = Narrow, 5 = Medium, 7 = Wide) | 3 |
| Leaf Color (at 5-leaf stage) (1 = Light Green, 2 = Medium Green, 3 = Dark Green, 4 = Blue-Green) | 2 |
| Leaf Waxiness (1 = Absent or Very Weak, 3 = Weak, 5 = Medium, 7 = Strong, 9 = Very Strong) | 3 |
| Leaf Texture (1 = Smooth, 9 = Rough) | |
| Leaf Lobe Development (1 = Absent or Very Weak, 3 = Weak, 5 = Medium, 7 = Strong, 9 = Very Strong) | 4 |
| Leaf Lobe Number (count) | 4 |
| Leaf Lobe Shape (1 = Acute, 9 = Rounded) | |
| Petiole Length (lobed cultivars only) (3 = Short, 5 = Medium, 7 = Long) | 3 |
| Leaf Margin Shape (1 = Undulating, 2 = Rounded, 3 = Sharp) | 3 |
| Leaf Margin Indentation (observe fully developed upper stem leaves) (1 = Absent or Very Weak (very shallow), 3 = Weak (shallow), 5 = Medium, 7 = Strong (deep), 9 = Very Strong (very deep)) | 3 |
| Leaf Attachment to Stem (1 = Complete Clasping, 2 = Partial Clasping, 3 = Non-Clasping) | |
| AFTER FLOWERING | |
| Time to Flowering (days from planting to 50% of plants showing one or more open flowers) | 46 |
| Plant Height at Maturity (3 = Short, 5 = Medium, 7 = Tall) | |
| Plant Growth Habit (1 = Erect, 3 = Semi-Erect, 5 = Intermediate, 7 = Semi-Prostrate, 9 = Prostrate) | |
| Flower-Bud Location (1 = Buds above most recently opened flowers, 9=Buds below most recently opened flowers) | |
| Petal Color (on first day of flowering) (1 = White, 2 = Light Yellow, 3 = Medium Yellow, 4 = Dark Yellow, 5 = Orange, 6 = Other) | 3 |
| Petal Length (3 = Short, 5 = Medium, 7 = Long) | |
| Petal Width (3 = Narrow, 5 = Medium, 7 = Wide) | |
| Petal Spacing (1 = Open, 3 = Not Touching, 5 = Touching, 7 = Slight Overlap, 9 = Strong Overlap) | 4 |
| Anther Dotting (percentage at opening of flower) (1 = absent, 9 = present (percentage)) | |
| Anther Arrangement (observe fully open flower) (1 = Introrse (facing inward), 2 = Erect, 3 = Extrorse (facing outward)) | |
| Pod (silique) Length (1 = Short (<7 cm), 5 = Medium (7 to 10 cm), 9 = Long (>10 cm)) | 4 |
| Pod (silique) Width (3 = Narrow (3 mm), 5 = Medium (4 mm), 7 = Wide (5 mm)) | 5 |
| Pod (silique) Angle (1 = Erect, 3 = Semi-Erect, 5 = Horizontal, 7 = Slightly Drooping, 9 = Drooping) | 3 |
| Pod (silique) Beak Length (3 = Short, 5 = Medium, 7 = Long) | 3 |
| Pod Pedicel Length (3 = Short, 5 = Medium, 7 = Long) | 5 |
| Time to Maturity (days from planting to physiological maturity) | 77 |
| SEED | |
| Seed Coat Color (1 = Black, 2 = Brown, 3 = Tan, 4 = Yellow, 5 = Mixed (describe), 6 = Other (specify)) | 1 |
| Seed Coat Mucilage (1 = absent, 9 = present) | |
| Seed Weight (5%-6% moisture) (grams per 1,000 seeds) | |

TABLE 1-continued

Table 1. Variety Descriptions based on Morphological, Agronomic and Quality Traits
Morphological and Other Characteristics of Canola *Brassica napus* G00555

| Characteristic | Value |
| --- | --- |
| GRAIN QUALITY | |
| Oil Content (percentage, whole dry seed basis) | 42.74 |
| Fatty-Acid Composition (percentage of total fatty acids in seed oil) | 6.79 |
| Palmitic Acid (C16:0) | |
| Stearic acid (C18:0) | |
| Oleic Acid (C18:1) | |
| Linoleic Acid (C18:2) | |
| Linolenic Acid (C18:3) | |
| Erucic Acid (C22:1) | |
| Total Saturated Fats | |
| Protein Content (percentage in oil-free meal) | 47.38 |
| Protein Content (percentage in whole dried seed) | 27.13 |
| Cystine | |
| Cystosine | |
| Methionine | |
| Other (specify) | |
| Glucosinolate Content (μ moles of total glucosinolates per gram whole seed, 8.5% moisture) (1 = Very Low (<10 μmol per gram), 2 = Low (10-15 μmol per gram), 3 = Medium (15-20 μmol per gram), 4 = High (>20 μmol per gram)) | 15.21 |
| Chlorophyll Content (mg/kg seed, 8.5% moisture) (1 = Low (<8 ppm), 2 = Medium (8-15 ppm), 3 = High (>15 ppm)) | |

What is claimed:

1. A seed, plant, plant part or plant cell of canola variety G00555, representative seed of said variety having been deposited under ATCC accession number PTA-126282.

2. The seed, plant, plant part, or plant cell of claim 1, wherein the seed, plant, plant part, or plant cell is a plant part and wherein the plant part is an ovule or pollen.

3. An F1 hybrid *Brassica* seed of G00555 produced from the cross of the plant or plant part of claim 1 with a different *Brassica* plant.

4. An F1 hybrid *Brassica* plant or a plant part thereof produced by growing the canola seed of claim 3, wherein the plant part comprises at least one cell of the F1 hybrid *Brassica* plant.

5. A method for producing a second *Brassica* plant, the method comprising applying plant breeding techniques to the F1 plant or plant part of claim 4 to produce the second *Brassica* plant.

6. A method for producing a progeny *Brassica* seed, the method comprising (a) crossing an inducer variety with the plant or plant part of claim 4 or a plant produced therefrom to produce haploid seed, and (b) doubling the haploid seed thereby producing the progeny *Brassica* seed.

7. A method of making a commodity plant product comprising silage, carbohydrate, oil or protein, the method comprising producing the commodity plant product from the *Brassica* plant or plant part of claim 4.

8. A method of producing a *Brassica* seed derived from the variety G00555, the method comprising:
   a) crossing the plant of claim 1 with itself or a second plant to produce progeny seed; and
   b) growing the progeny seed to produce a progeny plant and crossing the progeny plant with itself or a different plant to produce *Brassica* seed derived from the variety G00555.

9. A method for producing nucleic acids, the method comprising isolating nucleic acids from the seed, plant, plant part, or plant cell of claim 1.

10. A converted seed, plant, plant part or plant cell of inbred canola variety G00555, representative seed of the canola variety G00555 having been deposited under ATCC accession number PTA-126282, wherein the converted seed, plant, plant part or plant cell comprises a locus conversion, and wherein the plant or a plant grown from the converted seed, plant part or plant cell comprises the locus conversion and otherwise comprises essentially all of the physiological and morphological characteristics of canola variety G00555 when grown under the same environmental conditions.

11. The converted seed, plant, plant part or plant cell of claim 10, wherein the locus conversion confers a property selected from the group consisting of male sterility, site-specific recombination, abiotic stress tolerance, altered phosphate, altered antioxidants, altered fatty acids, altered essential amino acids, altered carbohydrates, herbicide tolerance, insect resistance and disease resistance.

12. An F1 *Brassica* seed produced by crossing the plant or plant part of claim 10 with a different *Brassica* plant.

13. An F1 hybrid *Brassica* plant or plant part produced by growing the seed of claim 12, wherein the plant part comprises at least one cell of the F1 hybrid *Brassica* plant.

14. A method for producing a second *Brassica* plant, the method comprising applying plant breeding techniques to the plant or plant part of claim 13 to produce the second *Brassica* plant.

15. A method for producing a second *Brassica* plant or plant part, the method comprising doubling haploid seed generated from a cross of the plant or plant part of claim 13 with an inducer variety, thereby producing the second *Brassica* plant or plant part.

16. A method of making a commodity plant product comprising carbohydrate, silage, oil or protein, the method comprising producing the commodity plant product from the *Brassica* plant or plant part of claim 13.

17. A method for producing nucleic acids, the method comprising isolating nucleic acids from the seed, plant, plant part, or plant cell of claim 10.

18. An F1 hybrid seed produced by crossing a plant or plant part of inbred canola variety G00555, representative seed of the variety having been deposited under ATCC accession number PTA-126282 with a different *Brassica* plant, wherein inbred canola variety G00555 further comprises a transgene that is inherited by the seed, wherein the transgene was introduced into inbred canola variety G00555 by backcrossing or genetic transformation.

19. A method of producing progeny seed, the method comprising crossing a plant grown from the seed of claim 18 with itself or a second plant to produce progeny seed.

20. A method of making a commodity plant product comprising silage, carbohydrate, oil or protein, the method comprising producing the commodity plant product from an F1 plant grown from the seed of claim 18.

* * * * *